US011357759B2

(12) United States Patent
Sher et al.

(10) Patent No.: US 11,357,759 B2
(45) Date of Patent: Jun. 14, 2022

(54) COMPOSITION INCLUDING ADAM9 INHIBITOR AND THE USE THEREOF

(71) Applicant: China Medical University, Taichung (TW)

(72) Inventors: Yuh-Pyng Sher, Taichung (TW); Yang-Chang Wu, Taichung (TW); Juan-Cheng Yang, Taichung (TW); Ting-Ting Kuo, Taichung (TW); Chia-Chien Lo, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 64 days.

(21) Appl. No.: 16/759,924

(22) PCT Filed: Oct. 29, 2018

(86) PCT No.: PCT/US2018/057895
§ 371 (c)(1),
(2) Date: Apr. 28, 2020

(87) PCT Pub. No.: WO2019/084529
PCT Pub. Date: May 2, 2019

(65) Prior Publication Data
US 2021/0052562 A1 Feb. 25, 2021

Related U.S. Application Data

(60) Provisional application No. 62/578,519, filed on Oct. 29, 2017.

(51) Int. Cl.
| | | |
|---|---|---|
| *A61K 31/4439* | (2006.01) | |
| *A61P 35/04* | (2006.01) | |
| *A61K 31/427* | (2006.01) | |
| *A61K 31/4709* | (2006.01) | |

(52) U.S. Cl.
CPC ........ *A61K 31/4439* (2013.01); *A61K 31/427* (2013.01); *A61K 31/4709* (2013.01); *A61P 35/04* (2018.01)

(58) Field of Classification Search
CPC .... A61K 31/4439; A61K 31/427; A61P 35/04
See application file for complete search history.

(56) References Cited

U.S. PATENT DOCUMENTS

| | | |
|---|---|---|
| 5,037,834 A | 8/1991 | Brighty et al. |
| 2004/0092466 A1 | 5/2004 | Bennett et al. |
| 2009/0163545 A1 | 6/2009 | Goldfarb |
| 2010/0056530 A1 | 3/2010 | Aicher et al. |

FOREIGN PATENT DOCUMENTS

| | | |
|---|---|---|
| EP | 1785420 A1 | 5/2007 |
| WO | 2004024089 A2 | 3/2004 |
| WO | 2007041634 A1 | 4/2007 |
| WO | 2007053345 A1 | 5/2007 |
| WO | 2015172196 A1 | 11/2015 |

OTHER PUBLICATIONS

Michalsky, J. et al., "Some additional 4,4'-bis(aminoalkyl)-2,2' bithiazoles". Chemical Abstracts Service (CAS) Database, Accession No. 1955:77845, abstract (chemical substance first available in 1954).
Mochizuki, Satsuki et al., "ADAMs in cancer cell proliferation and progression", Cancer science, published on Mar. 8, 2007, vol. 98, issue 5, pp. 621-628, published by Japanese Cancer Association, Japan.
Russell, Stephanie et al., "Hit-to-Lead Optimization of a Novel Class of Potent, Broad-Spectrum Trypanosomacides", Journal of Medicinal Chemistry, published on Aug. 22, 2016, vol. 59, issue 21, pp. 9686-9720, published by American Chemical Society, United States.
Walczynski, Krzysziof et al., "Histamine H, receptor ligands Part II. Synthesis and in vitro pharmacology of 2-[2-(phenylamino)thiazol-4-yl]ethanamine and 2-(2-benzhydrylthiazol-4-yl)ethanamine derivatives", Il Farmaco, published on Nov. 23, 2000, vol. 55, issue 9-10, pp. 569-574, published by Elsevier Science S.A., France.

*Primary Examiner* — Kamal A Saeed

(57) ABSTRACT

The present disclosure relates to an ADAM9 inhibitor compound of formula (I), including salts, hydrates and stereoisomers thereof, compositions thereof, and methods of use therefor, including treating a person in need thereof with an effective amount of the compound or composition, and detecting a resultant improvement in the person's health or condition.

5 Claims, No Drawings

COMPOSITION INCLUDING ADAM9 INHIBITOR AND THE USE THEREOF

CROSS-REFERENCE TO RELATED APPLICATIONS

This application is the National Stage Entry of International Application No. PCT/US2018/057895, filed Oct. 29, 2018, which claims the benefit of priority to U.S. Provisional Application No. 62/578,519, filed on Oct. 29, 2017, the content of which is incorporated herein by reference.

BACKGROUND

Technical Field

The present disclosure relates to a compound and a composition thereof. More particularly, the present disclosure relates to a compound for inhibiting ADAM9 and a composition thereof.

Description of Related Art

ADAM9 (Disintegrin and metalloproteinase domain-containing protein 9) is overexpressed in tumors such as pancreatic, breast, prostate, and lung cancers; plays a potential causal role in tumorigenesis; and is considered as a better therapeutic target than other metalloproteases in cancers because its expression correlates to poor patient outcomes. ADAM9 participates in tumorigenesis due to its ability to cleave and release a number of molecules involved in cancer progression, and secretion of ADAM9 from stromal cells surrounding tumors promotes tumor development via neovascularization.

Our previous published results demonstrated that suppression of ADAM9 expression and its downstream signaling could significantly prolong survival time of lung tumor-bearing mice. As evident from clinical samples in lung cancer and breast cancer, we found that patients with a low expression level of ADAM9 in tumor specimens have longer survival time than that with high expression level of ADAM9. Furthermore, lack of phenotype in ADAM9 deficient mice suggests targeting ADAM9 in cancer treatment may be well tolerated.

Here we disclose the design and confirmation of small molecule compounds as ADAM9 inhibitors to block ADAM9 protease activity.

SUMMARY

The present disclosure provides methods and compositions for inhibiting ADAM9, treating cancer, and/or inhibiting the growth or metastasis of cancer cells. The present disclosure provides ADAM9 inhibitor compounds, including salts, hydrates and stereoisomers thereof, compositions thereof, and methods of use therefor, including treating a person in need thereof with an effective amount of the compound or composition, and detecting a resultant improvement in the person's health or condition.

In an aspect the present disclosure provides a method of inhibiting ADAM9, treating cancer, and/or inhibiting the growth or metastasis of cancer cells, comprising treating a person in need thereof with an ADAM9-inhibitor compound of formula I, or use of an ADAM9-inhibitor compound of formula I in the manufacture of a medicament for inhibiting ADAM9, treating cancer, and/or inhibiting the growth or metastasis of cancer cells,

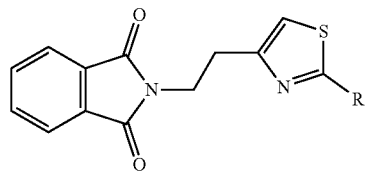

wherein:
R is a substituted or unsubstituted $C_1$-$C_{18}$ hydrocarbyl comprising 0-3 heteroatoms (N, S or O), or a heteroatom (N, S or O) substituted with a $C_1$-$C_{18}$ hydrocarbyl comprising 0-3 heteroatoms (N, S or O); and
R comprises a $C_5$-$C_{10}$ organocyclic;
or a pharmaceutically acceptable salt, hydrate or stereoisomer the compound.

In aspects the present disclosure provides a composition disclosed ADAM9-inhibitor compound of formula I coformulated with a different anticancer compound.

DETAILED DESCRIPTION

The following descriptions of particular embodiments and examples are provided by way of illustration and not by way of limitation. Those skilled in the art will readily recognize a variety of noncritical parameters that could be changed or modified to yield essentially similar results. The present disclosure provides myriad embodiments.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genera are recited as shorthand for a recitation of all members of the genus; for example, the recitation of ($C_1$-$C_3$) alkyl is shorthand for a recitation of all $C_1$-$C_3$ alkyls: methyl, ethyl and propyl, including isomers thereof.

The following words, phrases and symbols are generally intended to have the meanings as set forth below, except to the extent that the context in which they are used indicates otherwise. The following abbreviations and terms have the indicated meanings throughout.

The term "alkyl" refers to a hydrocarbon group selected from linear and branched saturated hydrocarbon groups of 1-18, or 1-12, or 1-6 carbon atoms. Examples of the alkyl group include methyl, ethyl,1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl,2-methyl-2-butyl,3-methyl-2-butyl,3-methyl-1-butyl,2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

Substituents are selected from: halogen, —R', —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)—NH, —NR'C(NH$_2$)NH, —NH—C(NH$_2$)NR', —S(O)R', —SO$_2$R', —SO$_2$NR'R", —NR"SO$_2$R, —CN and —NO$_2$, —N$_3$, —CH(Ph)$_2$, perfluoro(C$_1$-C$_4$)alkoxy and perfluoro(C$_1$-C$_4$)alkyl, in a number ranging from zero to three, with those groups having zero, one or two substituents being particularly preferred. R', R" and R'" each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl".

Preferred substituents are selected from: halogen, —R', —OR', —O, —NR'R", —SR', —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, perfluoro(C$_1$-C$_4$)alkoxy and perfluoro(C$_1$-C$_4$)alkyl, where R' and R" are as defined above.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH—C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the present disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof that has, for example, cancer.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent L-R$^4$" herein includes from 1 to 4, such as from 1 to 3, further as 1 or 2, substituents selected from the list of L-R$^4$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The at least one additional therapeutic agent can be, for example, selected from anti-hyperproliferative, anti-cancer, and chemotherapeutic agents. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gamma1I and calicheamicin omega1I (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethyihydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone), panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with a subject compound and stereoisomers thereof, and pharmaceutically acceptable salt thereof may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrastemal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

The subject compounds and stereoisomers thereof, and pharmaceutically acceptable salts thereof disclosed herein can further be examined for efficacy in treating ADAM9 related diseases (conditions in which ADAM9 activity overexpressed in one or more cell types and is pathogenic) by in vivo assays. For example, the compound and/or the at least one pharmaceutically acceptable salts thereof disclosed herein can be administered to an animal (e.g., a mouse model) having ADAM9 related diseases and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, and other pharmaceutical acceptable expedients, for example, lactose, cellulose, and magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, and other pharmaceutical acceptable expedients, for example, colloidal silicon dioxide, magnesium stearate, microcrystalline cellulose, starch and lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, and other pharmaceutical acceptable expedients, for example, sodium carboxymethyl cellulose, sodium benzoate, sorbitol solution, U.S.P., and vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient, selected, for example, from other active ingredients known to be useful for treating ADAM9 related diseases in a patient.

Examples

Rational Design Strategy to Develop ADAM9 Inhibitors

To develop ADAM9 inhibitors a molecular docking approach was used to virtually screen compound structures that can fit into the catalytic site of ADAM9's metalloproteinase domain. In our previous study (Cancer Res 2014, 74:5229), we found that ADAM9 knockdown reduced both CDCP1 expression and CDCP1 cleavage through plasminogen activator-based pathway. Initially 11 compounds with a top 1% ranking were predicted to target the catalytic site of ADAM9 and then they were used to investigate their effect in regulation of CDCP1 and PAI-1 expression. We confirmed that representative compound 310 can structurally occupy the site, suppress CDCP1 cleavage and increase PAI-1 expression in Bm7 lung cancer cells. We also demonstrated that it reduced cell migration distance of Bm7 cells, as determined using CCD video cameras (AxioCam MRm, Zeiss, Jena, Germany) and the Track Point function of Image J software (NIH, Bethesda, Md., USA).

We chose compound 310 as the core structure and then choose their derivatives for further investigation (see, Table 1). The representative derivatives can reduce CDCP1 expression. We performed cytotoxicity assay to measure $IC_{50}$ value of these derivatives in lung cancer cells lines (see, Table 2). Preferred derivatives strongly reduced the $IC_{50}$ for the cytotoxicity of lung cancer cells in suspension culture compared to the original compound 310, such as 12W0271 and 6X0214.

We calculated the Ki (inhibitory constant) of potential ADAM9 inhibitors such as MMP inhibitor CGS27023A, and two 310 derivatives using Autodock v. 4.2. We found that both 310 derivatives have a lower Ki value than the MMP inhibitor in support of our contention that a lower concentration of an ADAM9 inhibitor provides the same inhibitory effect as a higher concentration of MMP inhibitor.

Specificity of ADAM9 Inhibitors

To measure the efficacy of ADAM9 inhibitors in suppression of ADAM9 enzymatic activity, we established an ELISA system using recombinant human ADAM9 and a fluorogenic peptide substrate (R&D system). Broad-spectrum metalloprotease inhibitor BB-94 was included as a positive control. Lead compounds of the ADAM9 inhibitor panel (12W0271 and 6X0214) decreased ADAM9 activity to a similar extent in a dose-dependent manner. However, they had no inhibitory effects in ADAM17. To evaluate the specificity of ADAM9 inhibitors, we performed a migration inhibition assay in control (shGFP) and ADAM9 knockdown (shADAM9) lung cancer cells in the presence of 25 µM of each compound. Representative compounds significantly reduced migration ability in Bm7-shGFP control cells. To ensure the generality of the compounds in blocking anoikis-resistance of cancer cells, we determined the $IC_{50}$ of representative compounds for anoikis (anchorage-free induced apoptosis) in cancer cell lines and leukocytes in anchorage-free culture conditions. These results indicate they can induce cell death under anchorage-free culture conditions and also provide good therapeutic effects in a breast cancer brain metastatic cell line (MDA-231brm). Plating efficiency of Bm7 treated with 20 µM ADAM9 inhibitor and TC1 cells treated with 10 µM ADAM9 inhibitor was shown. Control and ADAM9 knockout (KO) TC1 cells were treated with ADAM9 inhibitor for 24 hours and then stained with annexin V and PI. The apoptotic cells (Annexin V positive cells) are indicated as the percentage of gated cells from three independent experiments with mean±SD. The data demonstrate that ADAM9 inhibitors can significantly reduce the control lung cancer cell growth compared to ADAM9 silence cells by colony formation assay and induce cell apoptosis.

Moreover, we detected the $IC_{50}$ of ADAM9 inhibitors in pancreatic cancer cells and showed the ADAM9 inhibitors reduced the pancreatic cancer cell growth.

Consistent with our finding that ADAM9 knockdown reduced the TICs number of lung cancer cells, we found the sphere number in the ADAM9 inhibitor treatment group was significantly lower than that in the vehicle-treated group, indicating that these ADAM9 inhibitors can suppress TIC formation (*, P<0.05. **, P<0.01).

Efficacy to Reduce Metastasis in Cancer Animal Models: ADAM9 Inhibitors Act as an Anti-Tumor Agent for Lung Cancer and Breast Cancer.

To further evaluate the antitumor effects of ADAM9 inhibitors in vivo, we intravenously injected mouse lung cancer cell TC1 ($8\times10^5$) in immune competent C57BL/6 mice as lung metastastic models and treated them with representative ADAM9 inhibitors via subcutaneous route (10 mg/kg). ADAM9 inhibitor was injected once a day for 3 weeks, from Day 15 to Day 36. Whole lungs were removed to measure the weight of lung tumors on Day 39. We found the compounds can strongly reduce the whole lung weight representing the metastatic lung tumor compared to that in DMSO group. In addition, we subcutaneously transplanted mouse lung cancer TC1 cells ($1\times10^6$) in immunocompetent mice and treated them subcutaneously with 10 mg/kg ADAM9 inhibitor. ADAM9 inhibitor was injected once a day for 3 weeks from Day 15 to Day 26. We observed smaller tumor sizes in the treatment groups than the DMSO-treated (negative control) group, consistent with our observation in ADAM9 knockout TC1 tumor animal models. We also established a syngeneic orthotopic breast tumor animal model by transplanting 4T1-luc cells in mammary fat pad. Balb/c mice received mammary fat pad injection of $5\times10^4$ 4T1-luc cells (N=10 each group). ADAM9 inhibitor was injected subcutaneously with at 10 mg/kg once a day for 3 weeks from Day 14 to Day 35. We found strong signal of tumor metastasis in DMSO group as compared to the ADAM9 inhibitor treatment groups on day 34, despite similar tumor signal among the three groups on day 13 with an IVIS imaging system. Moreover, the survival curve demonstrated that our inhibitor treatments significantly prolonged the survival time compared with the control group. Taken together, our results demonstrate that our ADAM9 inhibitors had an antitumor effect in reducing metastases of lung and breast tumors.

To mimic the neo-adjuvant therapy of drugs with surgery in early stage cancer patients for clinical application, we further evaluated the antitumor effects of ADAM9 inhibitors with removal of primary breast tumor in orthotopic breast tumor model. We transplanted 4T1 breast cells ($5\times10^4$) in mammary fat pad and monitor the tumor size with IVIS imaging system, which the photo flux detected in tumor was proportional to tumor size (N=5 each group). We pre-treated mice with 10 mg/kg of ADAM9 inhibitor by subcutaneous injection before surgery and continually injected ADAM9 inhibitor after surgery. The primary breast tumors were removed on day 21 post cancer cell transplantation and showed the similar size in the two groups. Although primary breast tumors were removed, however, we found tumor recurrence in negative control group (NC) by detecting signals with IVIS. Notably, combined surgery and ADAM9 inhibitor treatment reduced lung metastasis compared to the surgery alone group (NC group) under image detection. The reduced lung metastases were confirmed in histological evaluation of lung specimens. The mice body weights from the two groups were in steady, indicating no severe toxicity after drug treatment. To further evaluate the toxicity of the compounds in animal treatment, blood samples from the two groups at different time points were collected to measure the plasma levels of liver aspartate aminotransferase (AST), alanine aminotransferase (ALT) and blood urea nitrogen (BUN) for monitoring the liver and kidney function. The levels of the three factors in the treated group were in normal range, indicating no liver or kidney toxicity. From these results, we demonstrated inhibition of ADAM9 activity by our ADAM9 inhibitors provides anti-tumor benefits, including decreasing relapse after surgery.

To compare the therapeutic effect of the inhibitors to chemotherapy agent doxorubicin in breast cancer treatment, we treated mice with 12W0271 or doxorubicin as adjuvant therapy after surgery of primary breast tumors. Balb/c mice received mammary fat pad injection of $5\times10^4$ 4T1-luc cells. ADAM9 inhibitor was subcutaneously injected at 10 mg/kg once a day, 5 times per week for total 12 times. Doxorubicin was intraperitoneally injected at 1 mg/kg, once a day, 5 times per week for total 12 times. The surgical removal of tumors showed the similar size in the three groups. IVIS image on one day after surgery demonstrated successful surgery to remove primary tumors without any signal detection. This breast tumor animal model is a clinically relevant triple negative breast cancer with poor outcome. In doxorubicin treatment, only one mouse (12.5%) had complete response with no relapse. Body weight of survived mice in doxorubicin and 12W0271 groups was determined on day 140. Dash line indicates average body weight in normal mice. Notably, three mice (37.5%) had no relapse under 12W0271 treatment over 333 days, and they showed healthy condition with bigger body size than the survival one in doxorubicin group, indicating 12W0271 can be safe for long term treatment.

To investigate the synergistic effect of chemotherapy drugs and ADAM9 inhibitors, we measured the cytotoxicity of individual and combination of cisplatin and 12W0271 for 3 days in TC1 cells by MTT. The combination index (CI) curve analysis showed the value <1 indicates the synergistic effect of combined cisplatin and 12W0271 treatment. In metastatic lung tumor animal models by intravenously injection of TC1 lung cancer cells, we found cisplatin treatment significantly prolonged survival time but ADAM9 inhibitor had no effect. ADAM9 inhibitor (4 mg/kg) was intravenous injected twice a week for 4 weeks and cisplatin (1.5 mg/kg) was intraperitoneal injected twice a week for 4 weeks. Notably, combination of cisplatin and ADAM9 inhibitors significantly reduced lung cancer metastasis and prolonged mice survival time longer than that in the cisplatin treatment group, indicating a synergistic effect on combination of cisplatin and ADAM9 inhibitor in vivo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

TABLE 1

ADAM9 Inhibitors

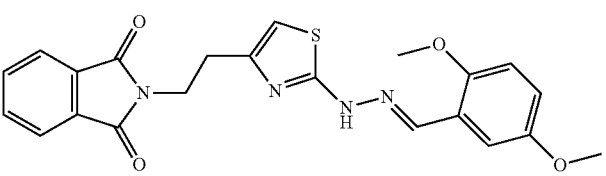 [SMILES: COc1ccc(OC)c(/C=N/Nc2nc(CCN3C(=O)c4ccccc4C3=O)cs2)c1]

2X-0295

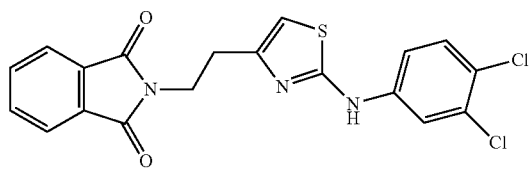 [SMILES: O=C1c2ccccc2C(=O)N1CCc1csc(Nc2ccc(Cl)c(Cl)c2)n1]

2X-0336

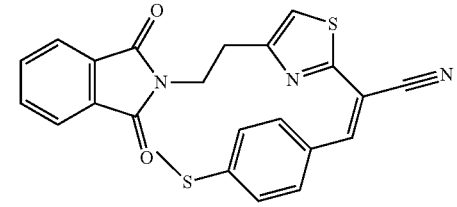 [SMILES: CSc1ccc(/C=C(/C#N)c2nc(CCN3C(=O)c4ccccc4C3=O)cs2)cc1]

4X-0296

TABLE 1-continued
ADAM9 Inhibitors
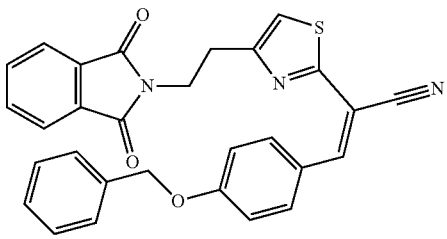 [SMILES: N#C/C(=C/c1ccc(OCc2ccccc2)cc1)c1nc(CCN2C(=O)c3ccccc3C2=O)cs1]
4X-0301
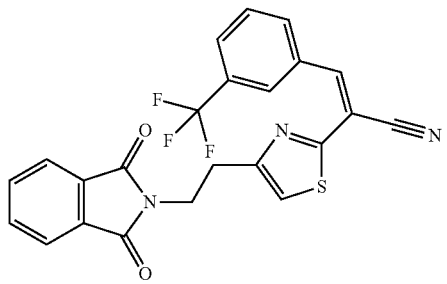 [SMILES: N#C/C(=C/c1cccc(C(F)(F)F)c1)c1nc(CCN2C(=O)c3ccccc3C2=O)cs1]
4X-0302
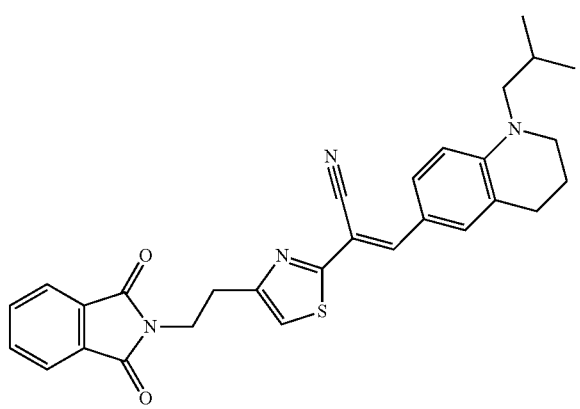 [SMILES: CC(C)CN1CCCc2cc(/C=C(\C#N)c3nc(CCN4C(=O)c5ccccc5C4=O)cs3)ccc21]
4X-0311
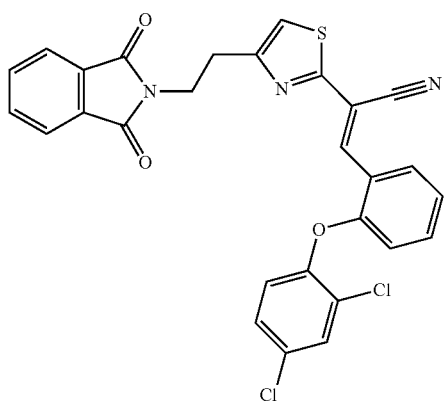 [SMILES: N#C/C(=C\c1ccccc1Oc1ccc(Cl)cc1Cl)c1nc(CCN2C(=O)c3ccccc3C2=O)cs1]
4X-0312
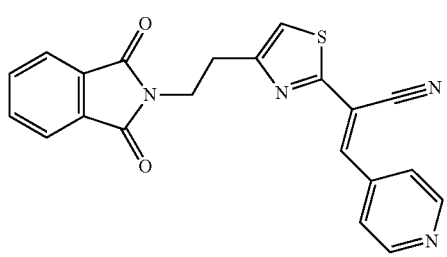 [SMILES: N#C/C(=C\c1ccncc1)c1nc(CCN2C(=O)c3ccccc3C2=O)cs1]
4X-0314

TABLE 1-continued
ADAM9 Inhibitors
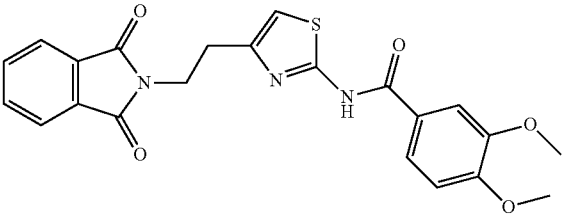 [SMILES: COc1ccc(C(=O)Nc2nc(CCN3C(=O)c4ccccc4C3=O)cs2)cc1OC] 5X-0314
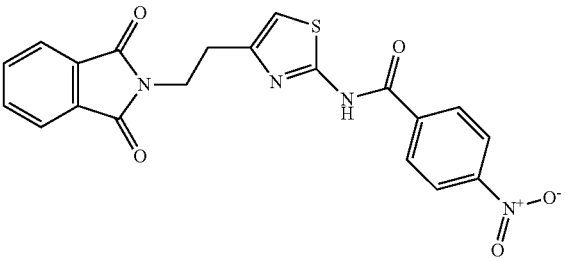 [SMILES: O=C(Nc1nc(CCN2C(=O)c3ccccc3C2=O)cs1)c1ccc([N+](=O)[O-])cc1] 6X-0202
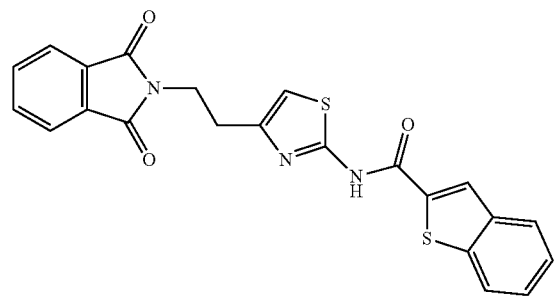 [SMILES: O=C(Nc1nc(CCN2C(=O)c3ccccc3C2=O)cs1)c1cc2ccccc2s1] 6X-0214
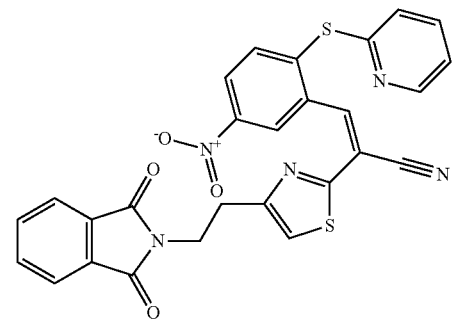 6X-0229
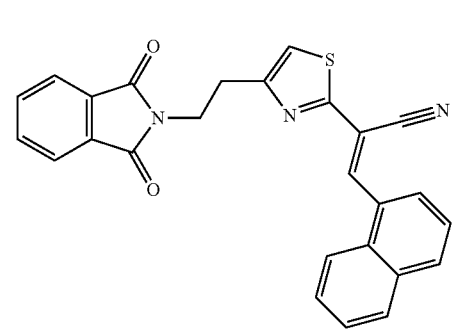 [SMILES: N#C/C(=C\c1cccc2ccccc12)c1nc(CCN2C(=O)c3ccccc3C2=O)cs1] 6X-0309

TABLE 1-continued
ADAM9 Inhibitors
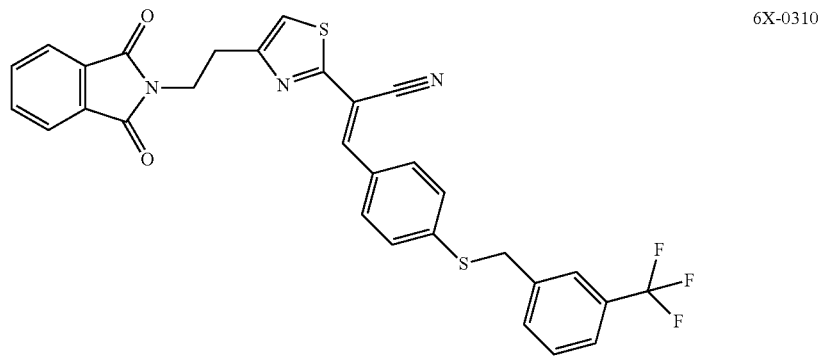 6X-0310
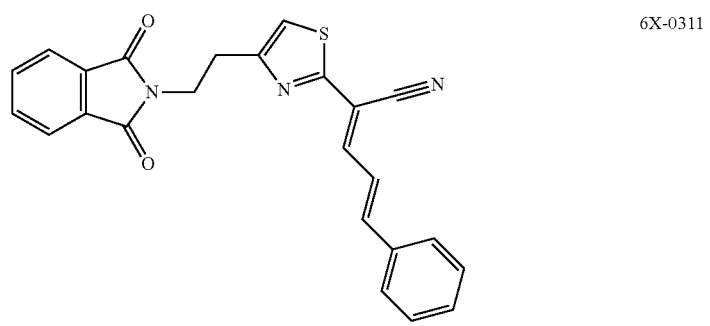 6X-0311
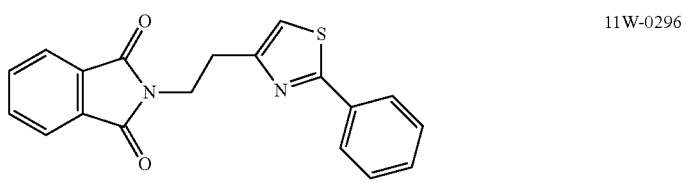 11W-0296
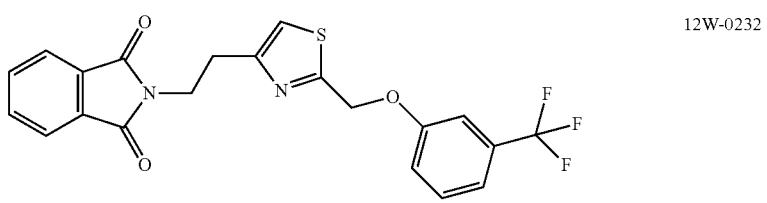 12W-0232
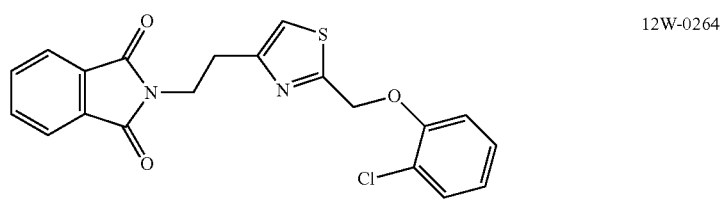 12W-0264
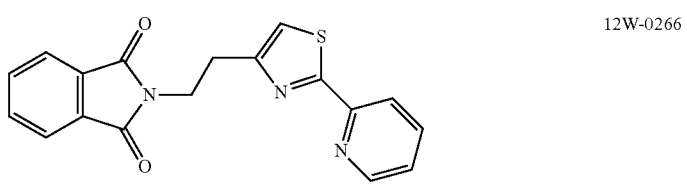 12W-0266

TABLE 1-continued
ADAM9 Inhibitors
| | |
|---|---|
| 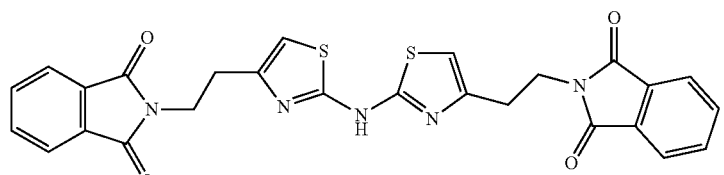 | 12W-0271 |
| 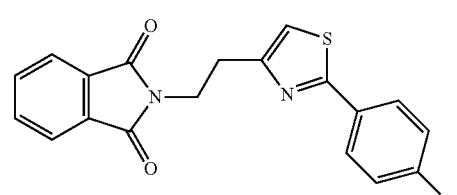 | 12W-0272 |
| 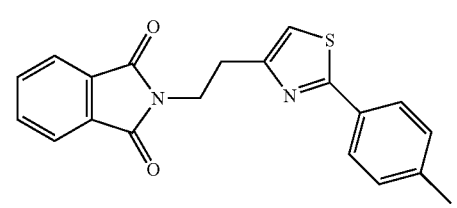 [SMILES: Cc1ccc(-c2nc(CCN3C(=O)c4ccccc4C3=O)cs2)cc1] | 12W-0274 |
| 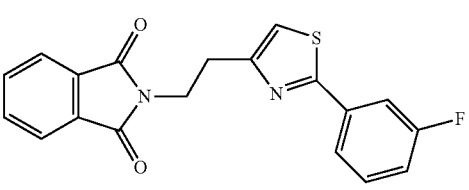 [SMILES: O=C1c2ccccc2C(=O)N1CCc1csc(-c2cccc(F)c2)n1] | 12W-0275 |
| 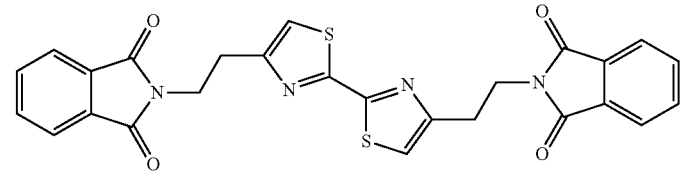 [SMILES: O=C1c2ccccc2C(=O)N1CCc1csc(-c2nc(CCN3C(=O)c4ccccc4C3=O)cs2)n1] | 12W-0290 |
| 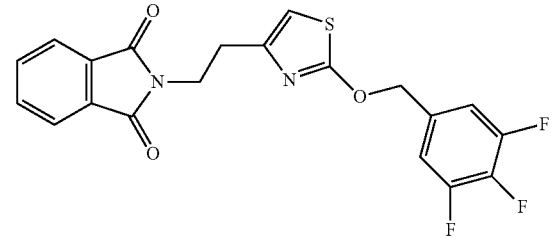 [SMILES: O=C1c2ccccc2C(=O)N1CCc1csc(OCc2cc(F)c(F)c(F)c2)n1] | 13W-0300 |
| 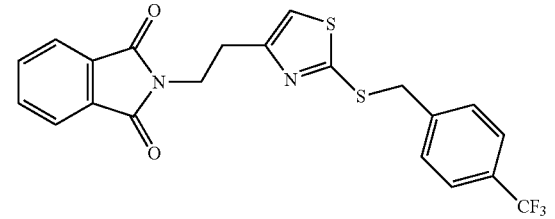 [SMILES: O=C1c2ccccc2C(=O)N1CCc1csc(SCc2ccc(C(F)(F)F)cc2)n1] | 13W-0301 |

TABLE 1-continued
ADAM9 Inhibitors
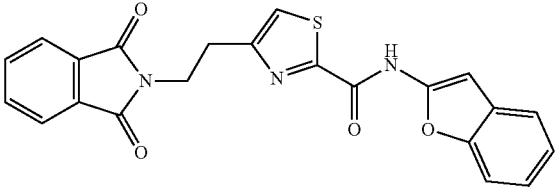 [SMILES: O=C(Nc1cc2ccccc2o1)c1nc(CCN2C(=O)c3ccccc3C2=O)cs1]
13W-0302
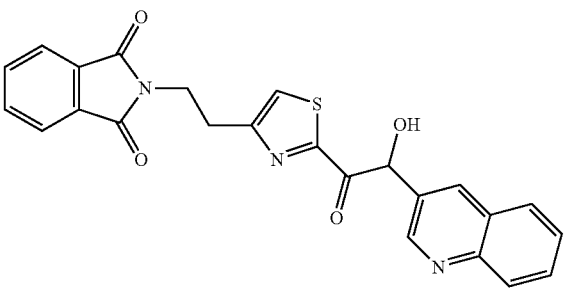 [SMILES: O=C(c1nc(CCN2C(=O)c3ccccc3C2=O)cs1)C(O)c1cnc2ccccc2c1]
13W-0303
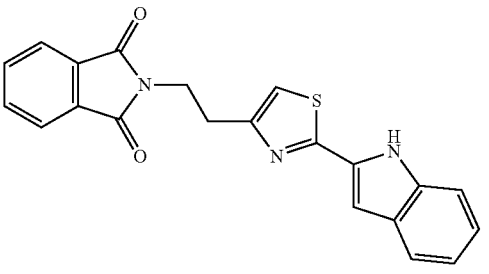 [SMILES: O=C1c2ccccc2C(=O)N1CCc1csc(-c2cc3ccccc3[nH]2)n1]
13W-0304
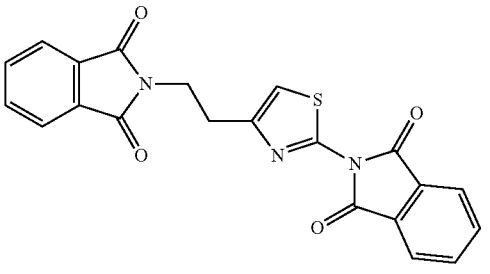 [SMILES: O=C1c2ccccc2C(=O)N1CCc1csc(N2C(=O)c3ccccc3C2=O)n1]
13W-0305
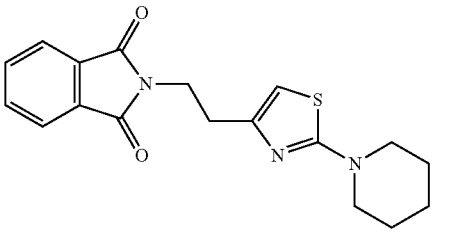 [SMILES: O=C1c2ccccc2C(=O)N1CCc1csc(N2CCCCC2)n1]
13W-0306
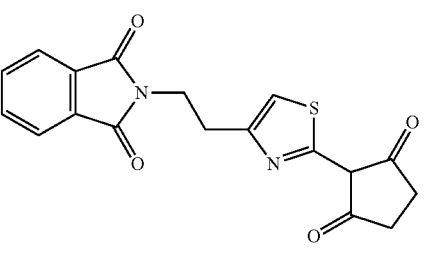 [SMILES: O=C1CCC(=O)C1c1nc(CCN2C(=O)c3ccccc3C2=O)cs1]
13W-0307

TABLE 2

Inhibitory activity in cancer cell; + indicates confirmed, significant inhibitor activity by IC$_{50}$; activities for 13W compounds were extrapolated.

| | 293 | HNOF | A549 | H1299 | TC1 | Bm7brmx2 | Bm7brmx2-1st | Bm7brmx2-2nd | 231-brm | PE10 WBC |
|---|---|---|---|---|---|---|---|---|---|---|
| 2X-0295 | + | + | + | + | + | + | + | + | | |
| 2X-0336 | + | + | + | + | + | + | + | + | | |
| 4X-0296 | + | + | + | + | + | + | + | + | | |
| 4X-0301 | + | + | + | + | + | + | + | + | | |
| 4X-0302 | + | + | + | + | + | + | + | + | | |
| 4X-0311 | + | + | + | + | + | + | + | + | | |
| 4X-0312 | + | + | + | + | + | + | + | + | | |
| 4X-0314 | + | + | + | + | + | + | + | + | | |
| 5X-0314 | + | + | + | + | + | + | + | + | | |
| 6X-0202 | + | + | + | + | + | + | + | + | | |
| 6X-0214 | + | + | + | + | + | + | + | + | + | + |
| 6X-0229 | + | + | + | + | + | + | + | + | | |
| 6X-0309 | + | + | + | + | + | + | + | + | | |
| 6X-0310 | + | + | + | + | + | + | + | + | | |
| 6X-0311 | + | + | + | + | + | + | + | + | | |
| 11W-0296 | + | + | + | + | + | + | + | + | | |
| 12W-0232 | + | + | + | + | + | + | + | + | | |
| 12W-0264 | + | + | + | + | + | + | + | + | | |
| 12W-0266 | + | + | + | + | + | + | + | + | | |
| 12W-0271 | + | + | + | + | + | + | + | + | + | + |
| 12W-0272 | + | + | + | + | + | + | + | + | | |
| 12W-0274 | + | + | + | + | + | + | + | + | | |
| 12W-0275 | + | + | + | + | + | + | + | + | | |
| 12W-0290 | + | + | + | + | + | + | + | + | | |
| 13W-0300 | + | + | + | + | + | + | + | + | | |
| 13W-0301 | + | + | + | + | + | + | + | + | | |
| 13W-0302 | + | + | + | + | + | + | + | + | | |
| 13W-0303 | + | + | + | + | + | + | + | + | | |
| 13W-0304 | + | + | + | + | + | + | + | + | | |
| 13W-0305 | + | + | + | + | + | + | + | + | | |
| 13W-0306 | + | + | + | + | + | + | + | + | | |
| 13W-0307 | + | + | + | + | + | + | + | + | | |

Exemplary Synthetic Scheme

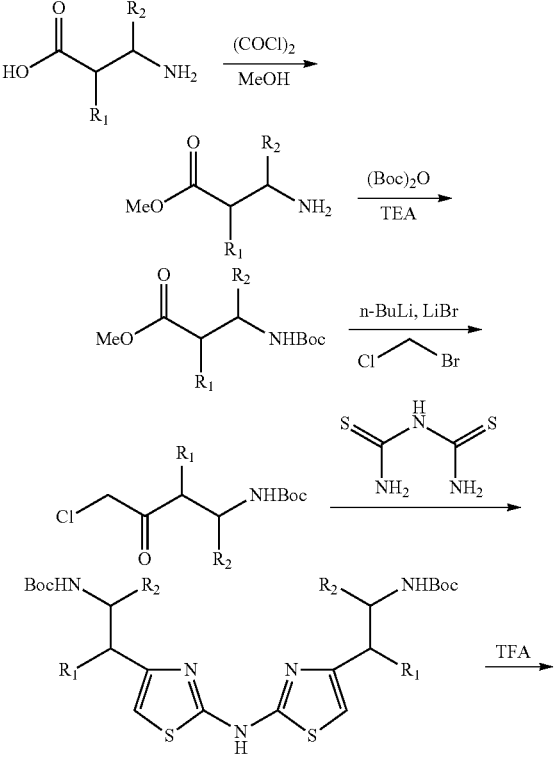

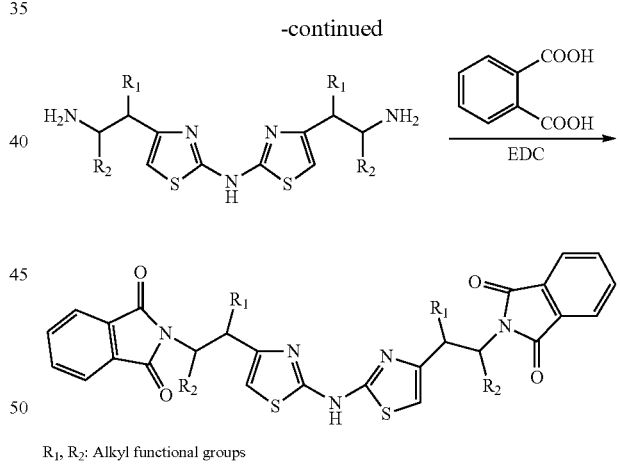

$R_1$, $R_2$: Alkyl functional groups

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A composition comprising a compound of formula I coformulated with a different anticancer compound,

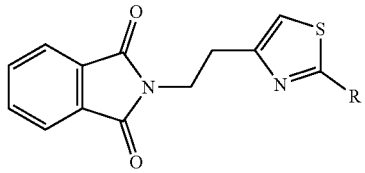

I wherein:

R is a substituted or unsubstituted phenyl, a substituted or unsubstituted $C_5$-$C_8$ heterocyclyl, a cyclopentanedione, $NHCOR_1$, $NHR_2$, $XR_3$, or a structure represent as formula (i):

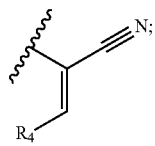

(i)

or a pharmaceutically acceptable salt, hydrate or stereoisomer the compound;

wherein $R_1$ is substituted or unsubstituted aryl comprising 0-3 heteroatoms (N, S or O); $R_2$ is 2-thiazol-4-yl-ethyl-isoindoline-1,3-dione, 1-(2,5-dimethoxyphenyl)-N-methylmethanimine or 4,5-dichlorobenzene; X is C, O, S or C=O, $R_3$ is substituted or unsubstituted phenyl or substituted or unsubstituted $C_8$-$C_9$ heterocyclyl; $R_4$ is optionally substituted aryl comprising 0-3 heteroatoms (N, S or O).

2. The composition of claim 1 wherein R is $NHR_2$, wherein $R_2$ is 2-thiazol-4-yl-ethyl-isoindoline-1,3-dione.

3. The composition of claim 1 wherein R is $NHCOR_1$, wherein $R_1$ is benzothiophene.

4. The composition of claim 1 wherein R is the structure represented as formula (i):

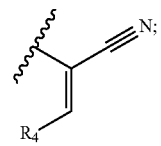

(i)

wherein $R_4$ is substituted phenyl.

5. The composition of claim 1 having a formula of the following table:

| compound | structural formula |
|---|---|
| 2X-0295 | |
| 2X-0336 | |
| 4X-0296 | |
| 4X-0301 | |

-continued
| compound | structural formula |
|---|---|
| 4X-0302 | 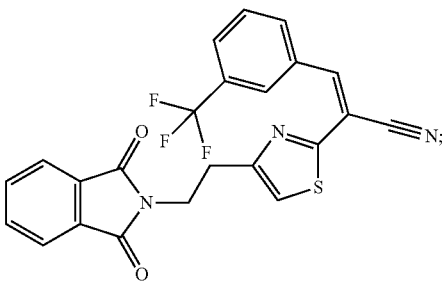 [SMILES: N#C/C(=C/c1cccc(C(F)(F)F)c1)c1nc(CCN2C(=O)c3ccccc3C2=O)cs1] |
| 4X-0311 | 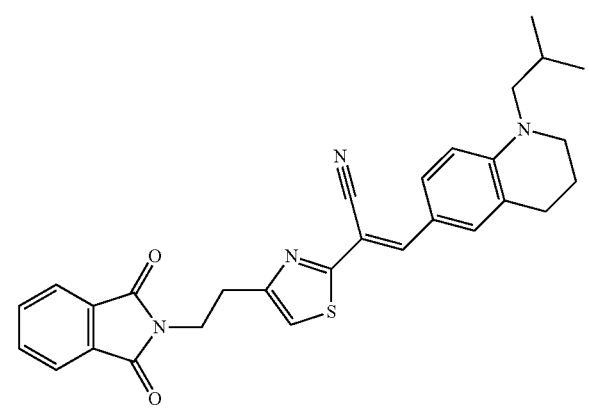 |
| 4X-0312 | 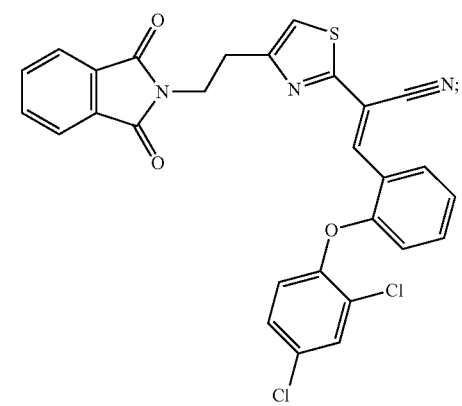 [SMILES: N#C/C(=C\c1ccccc1Oc1ccc(Cl)cc1Cl)c1nc(CCN2C(=O)c3ccccc3C2=O)cs1] |
| 4X-0314 | 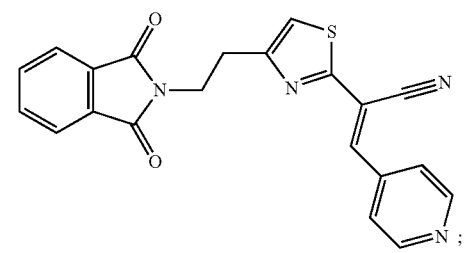 [SMILES: N#C/C(=C\c1ccncc1)c1nc(CCN2C(=O)c3ccccc3C2=O)cs1] |
| 5X-0314 | 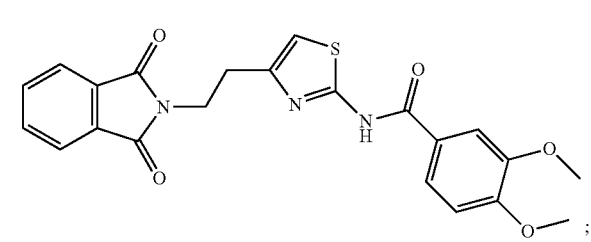 [SMILES: COc1ccc(C(=O)Nc2nc(CCN3C(=O)c4ccccc4C3=O)cs2)cc1OC] |

-continued

| compound | structural formula |
|---|---|
| 6X-0202 | |
| 6X-0214 | |
| 6X-0229 | |
| 6X-0309 | |
| 6X-0310 | |

-continued

| compound | structural formula |
|---|---|
| 6X-0311 | |
| 11W-0296 | |
| 12W-0232 | |
| 12W-0264 | |
| 12W-0266 | |
| 12W-0271 | |
| 12W-0272 | |

| compound | structural formula |
|---|---|
| 12W-0274 | 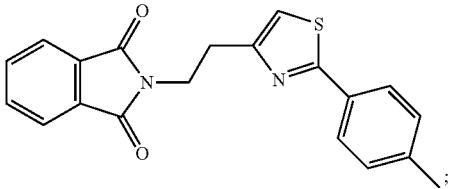 [SMILES: Cc1ccc(-c2nc(CCN3C(=O)c4ccccc4C3=O)cs2)cc1] |
| 12W-0275 | 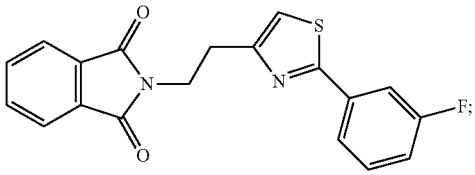 [SMILES: O=C1c2ccccc2C(=O)N1CCc1csc(-c2cccc(F)c2)n1] |
| 12W-0290 | 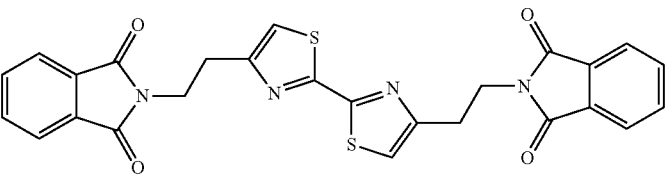 |
| 13W-0300 | 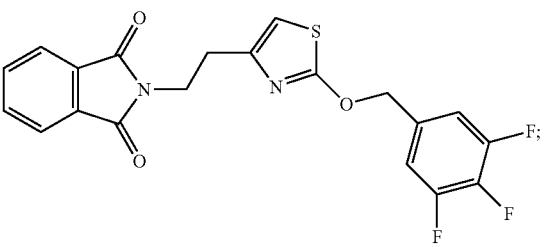 [SMILES: O=C1c2ccccc2C(=O)N1CCc1csc(OCc2cc(F)c(F)c(F)c2)n1] |
| 13W-0301 | 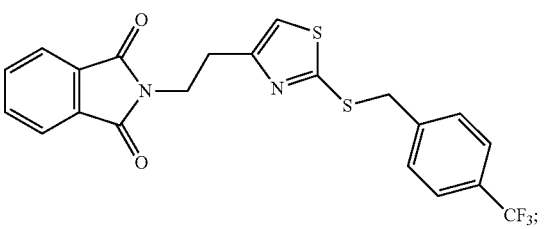 [SMILES: O=C1c2ccccc2C(=O)N1CCc1csc(SCc2ccc(C(F)(F)F)cc2)n1] |
| 13W-0302 | 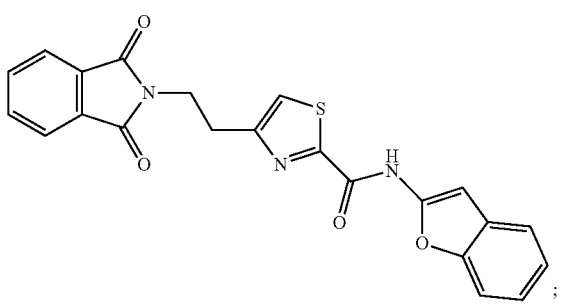 [SMILES: O=C(Nc1cc2ccccc2o1)c1nc(CCN2C(=O)c3ccccc3C2=O)cs1] |

-continued
| compound | structural formula |
|---|---|
| 13W-0303 | 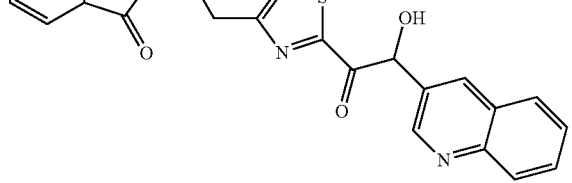 |
| 13W-0304 | 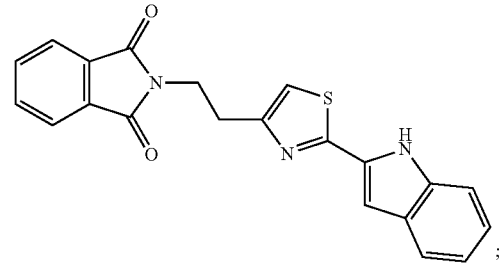 [SMILES: O=C1c2ccccc2C(=O)N1CCc1csc(-c2cc3ccccc3[nH]2)n1] |
| 13W-0305 | 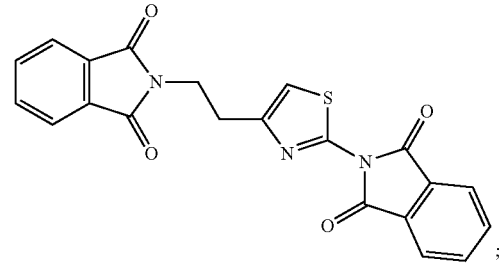 [SMILES: O=C1c2ccccc2C(=O)N1CCc1csc(N2C(=O)c3ccccc3C2=O)n1] |
| 13W-0306 | 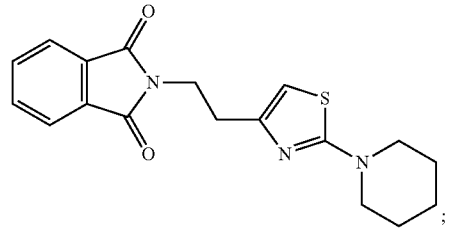 [SMILES: O=C1c2ccccc2C(=O)N1CCc1csc(N2CCCCC2)n1] |
| 13W-0307 | 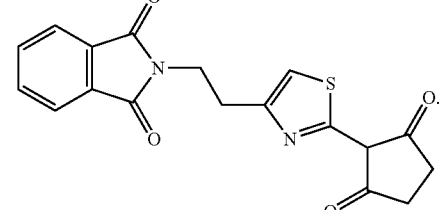 |
* * * * *